United States Patent
Khandal et al.

(10) Patent No.: US 8,586,646 B2
(45) Date of Patent: Nov. 19, 2013

(54) BARIUM CONTAINING NOVEL POLYACRYLATE FOR OPTICAL APPLICATIONS

(75) Inventors: Rakesh Kumar Khandal, Delhi (IN); Amita Malik, Delhi (IN); Geetha Seshadri, Delhi (IN); Mukti Tyagi, Delhi (IN)

(73) Assignee: Shriram Institute for Industrial Research, Delhi (IN)

( * ) Notice: Subject to any disclaimer, the term of this patent is extended or adjusted under 35 U.S.C. 154(b) by 446 days.

(21) Appl. No.: 12/303,645

(22) PCT Filed: Mar. 9, 2007

(86) PCT No.: PCT/IN2007/000097
§ 371 (c)(1),
(2), (4) Date: Feb. 24, 2009

(87) PCT Pub. No.: WO2007/141802
PCT Pub. Date: Dec. 13, 2007

(65) Prior Publication Data
US 2010/0234487 A1   Sep. 16, 2010

(30) Foreign Application Priority Data
Jun. 5, 2006 (IN) .............................. 1340/DEL/06

(51) Int. Cl.
*C08F 2/50* (2006.01)
*C08J 3/28* (2006.01)
(52) U.S. Cl.
USPC ................ 522/178; 522/71; 522/81; 522/182
(58) Field of Classification Search
USPC .............. 522/71, 81, 182, 178; 524/700, 779, 524/780
See application file for complete search history.

(56) References Cited

U.S. PATENT DOCUMENTS 4,585,841 A   4/1986   Eguchi et al.

*Primary Examiner* — Sanza McClendon
(74) *Attorney, Agent, or Firm* — The Webb Law Firm

(57) ABSTRACT

A process for the preparation of barium containing polyacrylates for optical and coating applications. The process consists in dispersing octahydrate of barium hydroxide in acrylic acid to form a monomer mixture. An aromatic carboxylic acid is added to the monomer mixture and then a cross linking agent is added thereto. Such a monomer mixture is subjected to the step of polymerization by gamma radiation.

8 Claims, No Drawings

BARIUM CONTAINING NOVEL POLYACRYLATE FOR OPTICAL APPLICATIONS

FIELD OF INVENTION

This invention relates to a process for the preparation of polymeric materials for use in ophthalmic applications such as polarized lenses, light waveguides, optical fibres and as varnish composition for coating films.

PRIOR ART

Plastic lenses have become popular in recent years for use in optical elements such as lenses. Resins which are widely used for the production of plastic lenses are diethylene glycol bisally 1 carbonate (1.50) and polyacrylates (1.45). Lenses prepared from them have a low refractive index than glass lenses (nd=1.52). In order to obtain equivalent properties to glass lenses, it is necessary to increase the center thickness, peripheral thickness, and the curvature of the lens as a result of which the lens becomes very thick.

Still other disadvantages are poor hardness and low impact strength.

OBJECT OF THE INVENTION

An object of this invention is to propose a process for the preparation of polymeric materials for use in optical lenses and coatings.

Another object of this invention is to propose a process for the preparation of polymeric materials for use in optical lenses and coatings which has a higher refractive index in comparison to that of the known art.

A still another object of this invention is to propose a process for the preparation of polymeric materials for use in optical lenses and coatings which has a comparatively higher hardness.

Yet another object of this invention is to propose a process for the preparation of polymeric materials for use in optical lenses and coatings which has a higher impact strength in comparison to the known art.

A further object of this invention is to propose a process for the preparation of polymeric materials for use in optical lenses and coatings which is efficient.

Further object and advantages of this invention will be more apparent from the ensuing description.

DESCRIPTION OF INVENTION

According to this invention there is provided a process for the preparation of plastic material for use in optical lenses and coatings comprising in the steps of:
a) Dispersing octahydrate of barium hydroxide in acrylic acid to form a monomer mixture;
b) adding an aromatic carboxylic acid selected from phenyl acetic acid or cinnamic acid to such a monomer mixture;
c) adding a cross linking such as styrene to the mixture of step c, and
d) and subjecting the mixture of step (c) to the step of polymerization by gamma radiation.

In accordance with this invention the process comprises in dispersing 17 to 19% by weight of octahydrate of barium hydroxide in acrylic acid. It has been found that if more than 19% by weight of octahydrate of barium hydroxide with respect to acrylic acid is added, then the mixture is no longer homogenous as some of the metal salt precipitates out. The mixture is stirred under a temperature of 25 to 30° C. to obtain a homogenous mixture.

Such a mixture has a refractive index of 1.442 upon addition 19% by weight of octahydrate barium hydroxide and 1.440 upon addition of 17% by weight of octahydrate barium hydroxide in comparison to a refractive index of 1.420 of acrylic acid.

To such a mixture, an aromatic carboxylic acid is added to increase the refractive index. The aromatic carboxylic acid is selected from phenyl acetic acid or cinnamic acid. It has been found that cinnamic acid imparts a yellow colour to the material. Thus, in the instance where colour is not desired, phenyl acetic acid is used for the lense and cinnamic acid for a coating composition.

It has been found that the presence of metal ions such as Barium is responsible for an increase in the impact strength. The presence of barium ions increases the refractive index only marginally.

As described hereinabove, octahydrate of barium hydroxide first added under continuous stirring to form a homogenous mixture. However, if the aromatic carboxylic acid is added first followed by addition of metal ions, then the dispersability decreases.

The aromatic carboxylic acid is also added under stirring conditions and at ambient temperature. Phenyl acetic acid is added in an amount of 9 to 11% by weight acrylic acid and cinnamic acid in an amount of 12 to 14% by weight of acrylic acid. If more than 11% by weight of phenyl acetic acid or 14% by weight of cinnamic acid is added to the mixture, there is no increase in the refractive index. However, if less than 9% by weight of phenyl acetic acid or 12% by weight of cinnamic acid is added to the mixture, then there is a reduction in the refractive index.

A cross linking agent such a styrene is finally added to the mixture and in an amount of 0.3 to 0.4 moles. Styrene also assists in improving the cross linking of the monomer units.

Such a mixture is subjected to the step of cast polymerization by using gamma radiation in the presence of cobalt 60 as the source. In the instance, where lenses is required, the mixture is subjected to the step of cast polymerization. The dose employed is 1.2 to 1.6 megarads.

Further objects and advantages of this invention will be more apparent from the ensuing examples, which are not intended to impart any restriction on the scope of the invention.

Example 1

5 gms of mixture containing octahydrate of barium hydroxide dispersed in acrylic acid and phenyl acetic acid was added to 3.12 gms of styrene. Such a mixture was poured into a mould made from two glass blanks and a gasket and subjected to gamma radiation in the presence of cobalt 60 at a, dose of 1.2 megarads.

The cast lens had the following properties:

| | |
|---|---|
| Refractive index | 1.55 |
| Transmittance | >90% |
| Shore D-hardness | 38 |
| Abbey no | 38 |
| Impact strength | Passes FDA standards |

Example 2

Example 1 was repeated except that cinnamic acid was used instead of phenyl acetic acid. The gamma radiation was carried out at a dosage of 2 megarods. The polymerized material was yellow coloured and more suitable as coating composition the following properties were obtained.

| | |
|---|---|
| Refractive index | 1.556 |
| Transmittance | >90% |
| Shore D-hardness | 38 |
| Abbey no | 38 |
| Impact strength | Passes FDA standards |

It is to be noted that the present invention is susceptible to modifications, adaptations and changes by those skilled in the art. Such variant embodiments employing the concepts and features of this invention are intended to be within the scope of the present invention, which is further set forth under the following claims:—

We claim:

1. A process for the preparation of plastic material for use in optical lenses and coatings comprising in the steps of:
   a) dispersing octahydrate of barium hydroxide in acrylic acid to form a monomer mixture;
   b) adding an aromatic carboxylic acid selected from phenyl acetic acid or cinnamic acid to such a monomer mixture;
   c) adding a cross linking agent such as styrene to the mixture of step (b), and
   d) subjecting the mixture of step (c) to the step of polymerization by gamma radiation,
   wherein said octahydrate of barium hydroxide is added to acrylic acid under stirring conditions and at ambient temperature.

2. A process as claimed in claim 1 wherein 17 to 19% by weight of barium hydroxide is added to acrylic acid.

3. A process as claimed in claim 1 wherein 9% to 11% by weight of phenyl acetic acid or 12 to 14% by weight of cinnamic acid is added to the mixture of acrylic acid and metal salt.

4. A process as claimed in claim 3 wherein said phenyl acetic acid or cinnamic acid is added to said mixture and stirred.

5. A process as claimed in claim 1 wherein the dose of radiation is 1.2 to 1.6 megarads.

6. A process as claimed in claim 1 wherein 9% to 11% by weight of phenyl acetic acid is added to the mixture of acrylic acid and metal salt.

7. A process as claimed in claim 1 wherein 12 to 14% by weight of cinnamic acid is added to the mixture of acrylic acid and metal salt.

8. A process for the preparation of plastic material for use in optical lenses and coatings comprising in the steps of:
   a) dispersing octahydrate of barium hydroxide in acrylic acid to form a monomer mixture, wherein barium hydroxide is added in an amount of 17 to 19% by weight;
   b) adding an aromatic carboxylic acid selected from phenyl acetic acid or cinnamic acid to such a monomer mixture, wherein 9% to 11% by weight of phenyl acetic acid or 12 to 14% by weight of cinnamic acid is added to the mixture;
   c) adding a cross linking agent such as styrene to the mixture of step (b), and
   d) subjecting the mixture of step (c) to the step of polymerization by gamma radiation,
   wherein said octahydrate of barium hydroxide is added to acrylic acid under stirring conditions and at ambient temperature.

* * * * *

UNITED STATES PATENT AND TRADEMARK OFFICE
CERTIFICATE OF CORRECTION

PATENT NO. : 8,586,646 B2  Page 1 of 1
APPLICATION NO. : 12/303645
DATED : November 19, 2013
INVENTOR(S) : Khandal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 651 days.

Signed and Sealed this
Twenty-second Day of September, 2015

Michelle K. Lee
*Director of the United States Patent and Trademark Office*